United States Patent [19]

Zarchy

[11] 4,282,741

[45] Aug. 11, 1981

[54] DEVICE AND METHOD FOR DETECTING ALKALI METALS

[75] Inventor: Andrew S. Zarchy, Clifton Park, N.Y.

[73] Assignee: General Electric Company, Schenectady, N.Y.

[21] Appl. No.: 33,257

[22] Filed: Apr. 25, 1979

[51] Int. Cl.³ .......................................... G01N 27/00
[52] U.S. Cl. ...................................... 73/23; 324/468
[58] Field of Search ............... 73/25, 23, 26; 324/468

[56] References Cited

U.S. PATENT DOCUMENTS

| 2,550,498 | 4/1951 | Rice | 324/468 |
| 2,742,585 | 4/1956 | Zemany | 324/468 X |
| 4,095,171 | 6/1978 | Bauerle et al. | 324/468 |

OTHER PUBLICATIONS

"Methods of Experimental Physics", by Hughes et al., vol. 4, pp. 393–397–Academic Press (1967).

Primary Examiner—James J. Gill
Attorney, Agent, or Firm—Robert R. Schroeder; James C. Davis, Jr.; Paul R. Webb, II

[57] ABSTRACT

A device for detecting alkali metals in gas streams includes a conduit defining a gas-flow cavity and a metalliferous filament having a work function of at least 5.6 ev extending transversely through the flow path. A heater heats the filament to ionize the alkali metals being detected. A perforated ion-collection member surrounds the filament to define an ionization-collection region. A high-voltage (HV) source develops a HV electrical field within the region, thereby effecting neutralization of the ionized metals contacted with the collection member. An ammeter generates a signal in response to the neutralization and proportional to the rate thereof. A detection method which can be performed by the device is also described.

2 Claims, 3 Drawing Figures

DEVICE AND METHOD FOR DETECTING ALKALI METALS

BACKGROUND OF THE INVENTION

The present invention relates to a device and method for detecting alkali metals in gas streams, and more particularly relates to detection of alkali metals present in trace amounts in gas streams over a wide range of pressure, including high pressure.

There are numerous instances where gases may contain alkali metals, the detection of which would prove useful. For example, in systems such as power plants including a gas turbine, it has been proposed to use gaseous products of combustion of coal or residual oil, gaseous products produced by gasification of coal, etc., as the motive fluid or gas stream for operating the gas turbine. One of the problems facing use of such gas for operating the gas turbine is that the gas typically contains alkali metals, which are found to deposit on working surfaces of the turbine with resulting detrimental effects (e.g. corrosion) on such surfaces.

It would be desirable to have a device and method for detecting the presence of alkali metals in such streams and more particularly desirable to have such device and method capable of detecting the presence of trace amounts of alkali metals in such streams over a wide pressure range, including high pressure.

It has now been found by practice of the present invention that in device and method embodiments thereof, presence of alkali metals, even in trace amounts, in such gas streams can be effectively and quantitatively detected over a wide range of gas pressure.

DESCRIPTION OF THE INVENTION

Generally stated, in one aspect, this invention provides a device for detecting the presence of one or more alkali metals present in a flowing gas, which may additionally contain electrically conductive species (e.g. moisture). The detection device comprises means (e.g. a conduit) defining a cavity adapted to conduct a flow of the gas along a flow path extending therethrough. A generally straight metalliferous filament having a work function ($\Phi$) of at least 5.3 ev (electron-volts) is disposed within the cavity and extends transversely through the gas flow path. A means, e.g. a low-voltage/high-current (LVHC) source electrically connected across the filament, is provided for heating the filament to a temperature (e.g. at least 700° C.) sufficient to ionize a substantial portion of the alkali metals. An electrically conductive ion-collection member including a cylindrically annular portion is provided with the annular portion surrounding the filament in closely spaced coaxial relationship therewith to define an ionization-collection (I-C) region of the cavity. The annular portion has a plurality of through-holes adapted to pass at least a portion of the flow therethrough. That is, the through-holes place the I-C region in flow communication with the portion of the cavity adjacent the exterior surface of the annular portion. A means, e.g. a high-voltage/direct-current (HVDC) source, is electrically connected at one end thereof through a first lead to the filament and connected at the other end thereof through a second lead to the ion-collection member for developing a high-voltage electrical field within the ionization-collection region. The field has lines of force extending from the filament through the flow path to the annular portion of the ion-collection member to effect contact of the ions with the ion collection member and neutralization of the ions thus contacted. Signal means, e.g. an ammeter, is operably associated with the second lead for generating a signal in response to the neutralization and proportional to the rate thereof.

In a preferred embodiment, the detecting device further includes means (e.g. a composite insulating-and-conducting assembly) for both (i) electrically insulating said collection member from said first lead and (ii) reducing leakage current through said signal-generating means.

A preferred composite insulating-and-conduction assembly includes (A) an electrically insulating (E-I) sleeve extending longitudinally of and peripherally about the first lead adjacent the end thereof adjoining the filament, (B) an electrically conductive low-resistance metallic sleeve extending longitudinally of and peripherally about the E-I sleeve, (C) an additional electrically insulating sleeve extending longitudinally of and peripherally about the metallic sleeve, and (D) means for electrically connecting the metallic sleeve to ground. The metallic sleeve preferably extends beyond at least one of the E-I sleeves toward the ionization-collection region.

In another aspect, the present invention provides an alkali metal detection method, which may be performed using the detection device.

BRIEF DESCRIPTION OF THE DRAWING

This invention will be better understood from the following detailed description taken with the accompanying drawing wherein the best mode contemplated for carrying out the invention is illustrated.

In the drawing, wherein like numerals refer to similar elements throughout.

DETAILED DESCRIPTION OF THE INVENTION AND MANNER AND PROCESS OF MAKING AND USING IT

Figure 1:
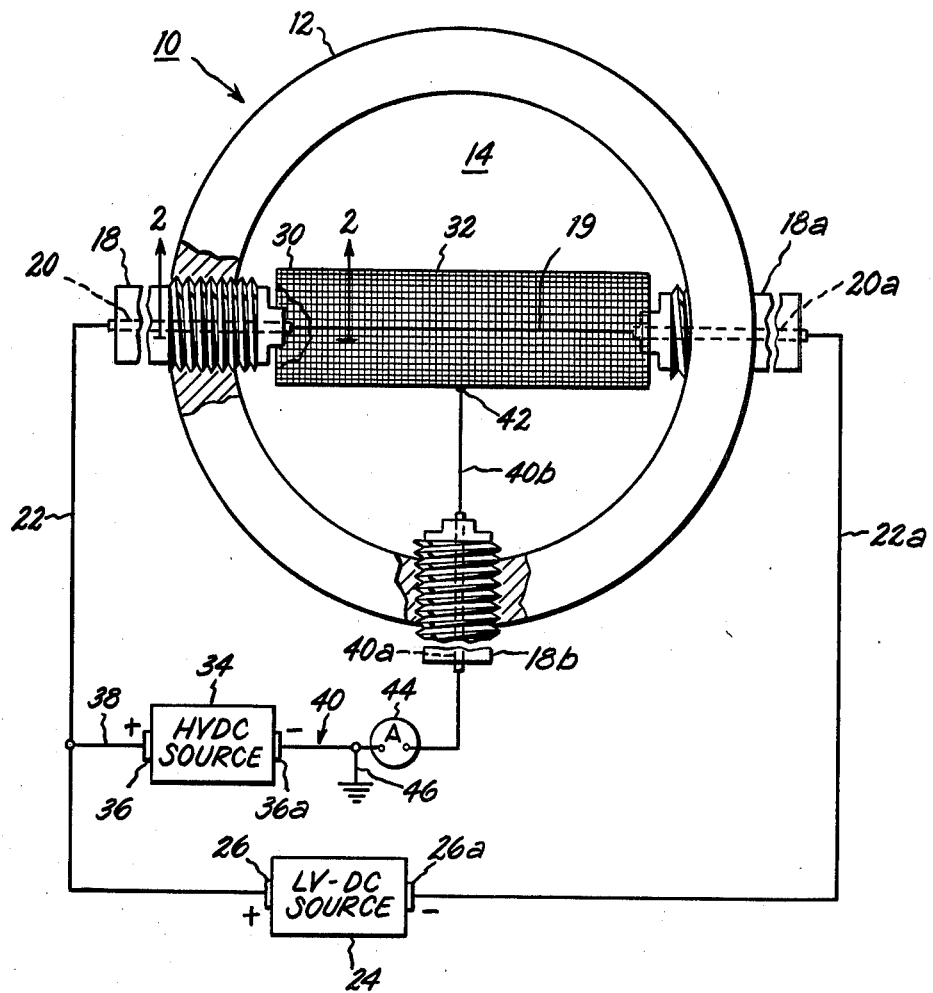
FIG. 1 is an end view, partly in section and with portions thereof removed, of a detection device in accordance with a preferred embodiment of this invention.

Referring now to the drawing and especially FIG. 1 thereof, there is shown alkali metal detection device 10 including conduit or pipe section 12 defining cavity 14 adapted to conduct a flow of gas therethrough along a flow path extending longitudinally thereof, e.g. upwardly through the plane of the drawing in FIG. 1. Support-and-connection assemblies 18 and 18a extend through holes in, and are carried by, the wall of pipe 12. Lead portions 20 and 20a of electrical leads 22 and 22a, respectively, extend through and are carried by, assemblies 18 and 18a, respectively. Opposite ends of electrically conductive metalliferous filament 19 having a work function ($\Phi$) of at least 5.3 ev are electrically connected to, and supported by, ends of the lead portions, as by silver soldering. LVHC source 24 (a low-voltage high-current source) is electrically connected at its positive terminal 26 to lead 22 and at its negative terminal 26a to lead 22a. The LVHC source preferably has sufficient power output to heat the filament to a temperature (e.g., at least 700° C.) sufficient to ionize a substantial portion of the alkali metal particles brought into contact or other ionizing association with the filament. For example, source 24 may have a voltage output of about 3 to 10 volts, with the filament and leads 22 and 22a being of sufficiently low resistance to conduct a sufficiently high current at such voltage to achieve the requisite filament temperature.

Electrically conductive (E-C) ion-collection member 30 includes E-C cylindrically annular portion 32 surrounding the filament 19 in closely spaced coaxial relationship therewith, thereby defining an ionization-collection region within the cavity and cylindrically enveloped by the annular portion. The annular portion may be a screen or grid, preferably of type 316 stainless steel, and having a plurality of holes 33 radially extending therethrough, the holes being adapted (e.g. sufficient in number and size) to pass at least a portion of the gas flow therethrough. For best results, such holes are preferably distributed uniformly throughout the annular portion of the ion-collection member. For simplicity, the annular portion of the ion-collection member is hereinafter referred to as the screen, it being recognized that other structures within the scope of the foregoing description may be employed.

HVDC source 34 (a high-voltage direct-current source) is electrically connected at positive end 36 thereof via branch 38 of lead 22 (and through portion 20 thereof) to an end of filament 19 as described above for the LVHC source. The HVDC source is connected at its negative end 36a through an additional electrical lead 40 to screen 32. Portion 40a of lead 40 extends through and is carried by support-and-connection assembly 18b, which is carried by wall 12, and portion 40b of such lead extends from an inner end of lead portion 40a to a suitable electrical connection 42 (e.g. silver solder) provided on the screen. The HVDC source may be adapted to provide an output voltage of from about 200 volts or less to about 1000 volts or more, preferably from about 300 to about 900 volts, e.g. about 600 volts. When energized, the HVDC source develops a high-voltage electrical field within the ionization-collection region bordered cylindrically by the screen 32. The field has lines of force extending radially outwardly from the filament along substantially its entire length through the flow path to screen 32. This field affects alkali-metal-containing positive ions generated from alkali metal atoms or other alkali-metal-containing ionizable species which are impinged on the filament by flow of gas containing same through the cavity while the filament is maintained at the above-described temperature. The field effects contact of at least a portion of such ions with the screen 32 and neutralization of the screen-contacted ions.

Ammeter 44 electrically interposed in series with legs of lead 40 generates a signal responsive to the neutralization, which signal is found to be proportional to the rate thereof. Although an ammeter is preferably included, any suitable current-indicating meter or other means operably associated with the lead 40 for generating a signal of such character may be employed. Lead 40 preferably includes branch 46 connecting this lead to ground, the branch extending from a node in the lead between the ammeter and the negative end of the HVDC source.

Screen 32 is provided at its open opposite ends with supports 48 (one shown—FIG. 2) carried by adjacent support-and-connection assemblies 18 and 18a, respectively, which are adapted to electrically insulate the screen from leads 22 and 22a (and filament 16). Supports 48 are preferably brass rings or discs, although other suitable support structures may be employed.

The structure of assemblies 18a and 18b may be identical to the structure of assembly 18, which includes a composite insulating-and-conducting system 50 (FIG. 2), the system being interposed mechanically and electrically between lead portion 20 and screen 32. Hereinafter, for simplicity, the composite insulator-conductor system is referred to as the CIC system. The preferred CIC system includes (a) inner electrically insulating high-resistance sleeve 52 extending longitudinally of and peripherally about at least the filament-adjoining end of lead portion 20; (b) an electrically conductive low-resistance metallic sleeve 54 extending longitudinally of and peripherally about such end of the insulating sleeve 52, with the sleeve 54 preferably extending beyond such end thereof; and (c) outer electrically insulating high-resistance sleeve 56 extending longitudinally of and peripherally about the low-resistance sleeve 54. As used herein, the terms "high-resistance" and "low-resistance" mean relatively high and relatively low electrical resistance, respectively. The inner insulating sleeve 52 is preferably of ceramic, although other high-resistance insulating material may be employed for this member. The outer insulating sleeve 56 is preferably of polytetra-fluoroethylene (hereinafter PTFE), although other high-resistance insulating material may be employed for this member. For simplicity, the sleeves 52 and 56 are sometimes referred to herein as the ceramic sleeve and the PTFE sleeve, respectively.

The support ring 48 is preferably carried in a recess provided in the PTFE sleeve, with the outer periphery of the ring preferably welded to the screen 32. Other suitable means for carrying and attaching the support may be employed. Means for electrically grounding metallic sleeve 54 (preferably of type 316 Stainless Steel) is provided, preferably in the form of electrically conductive low-resistance body 58 having a hollow core therethrough defined by inner surface 60 thereof. The body (preferably of stainless steel), is connected electrically, in turn, to ground by any suitable means, including, for example, pipe 12 per se where the pipe is formed of electrically conductive material, e.g. metal, the pipe being connected to ground potential via any suitable electrical lead (not shown).

The particular material of ceramic sleeve 52 is selected such that the sleeve has a high bulk resistivity or resistance, thereby effectively insulating the high voltage lead extending therethrough from electrically conductive structure at substantially lower electrical potential disposed outwardly thereof. However, in a number of critically important applications, it is found that moisture contained in the gas is deposited on the exposed surface of the ceramic sleeve, resulting in significantly decreasing the resistance of the exposed surface thereof, thereby allowing current to flow along such surface even though current is effectively precluded from flowing through the ceramic sleeve. In the absence of the metallic sleeve 54 and PTFE sleeve 56, such current (hereinafter referred to as leakage current) would flow from the high voltage conductor (lead 20 in the illustrated embodiment) to the screen. Such leakage current would be included in the total current measured by the ammeter, typically resulting in a widely varying component of the total measured current and thereby resulting in apparent but inaccurate indications of the amount of alkali metal(s) present in the flowing gas. The CIC assembly provides a solution to this problem by providing the metallic sleeve and associated grounding circuitry, which is selected to have a substantially lower resistance than the resistance in the ammeter-containing circuit portion. The resistance of the ammeter may be, for example, in the range from about 1000 to 1,000,000 ohms. The resistance of the leakage current circuit (i.e. metallic sleeve 54 and the grounding means therefor) will typically not be more than about 1 ohm. As a result of such different resistance, the CIC system effectively directs at least a substantial portion of the leakage current away from the ammeter.

The PTFE sleeve has a substantially high bulk resistivity and a surface resistivity which is not appreciably decreased by deposition thereon of moisture and other compositions which substantially decrease the surface resistivity of the ceramic sleeve material.

Figure 2:
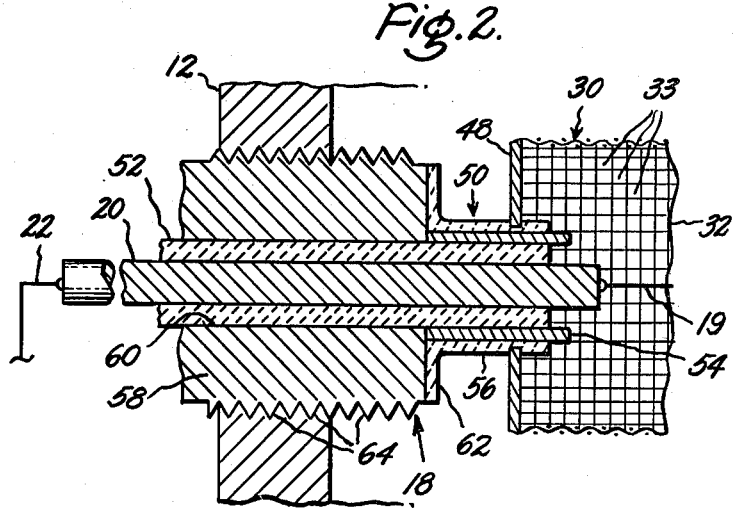
FIG. 2 is a sectional view taken on line 2-2 of FIG. 1.

Although the CIC system may be employed with other body structures, the body structure shown conveniently provides effective means for both supporting the components of the ionization-collection region and connecting the leads extending therefrom to the HVDC source and the LVHC source. The end portion of body 58 shown in FIG. 1 and FIG. 2 is carried by the wall of the conduit or pipe 12 (in holes therethrough) such that the body core extends through the wall and terminates within the cavity. As indicated above, a portion of lead 20 extends axially through the hollow core. The ceramic sleeve 52 has its inner surface surrounding such portion of the first lead in surface-to-surface contact therewith and has its outer surface in contact with core-defining surface 60 of the body. The ceramic sleeve and a portion of the first lead define a first insulator-lead structure having an extension projecting beyond the body portion toward the ionization-collection region, with the ceramic sleeve end portion included in such extension and forming a part of the CIC system.

The metallic sleeve 54 preferably projects beyond the ends of both insulating sleeves 52 and 56 (as illustrated), thereby substantially minimizing risk of direct bridging between the insulating sleeves, as may result for example by deposition of moisture at the free ends thereof.

The PTFE sleeve may be provided with a flange or lip 62 fitting flush against the inner end of body 58, thereby providing electrical insulation between the adjacent support 48 and the body. Preferably, the body extends inwardly from the inner surface of wall 12, which is spaced a suitable distance (e.g. 2 inches or more) from the support in such arrangement to electrically insulate the ion-collection member from the pipe. The body may be secured to the wall by any suitable securing means, e.g. threads 64 provided on the body and mating threads in the hole of the wall through which the body extends.

The insulating sleeve 56 may be of PTFE, polyethylene, ceramic or the like. PTFE is preferred for service temperatures of sleeve 56 below 500° F. At 500° F. or higher service temperature, ceramic is preferred.

As a general preference, the various leads are of copper.

The metalliferous filament may be a filament formed of metal, metal oxide, or metal alloy provided that the filament has a work function of at least 5.3 ev. Suitable materials of which the filament may be formed include, for example, platinum (Pt), tungsten (W), rheninm (Re), palladium (Pd), and oxides and alloys of the foregoing which have the requisite minimum work function. The filament is preferably of platinum. For best results, the platinum should be substantially free of alkali metals, e.g. less than 0.5% by weight alkali metal.

The detector device has particular application to detecting alkali metals present, in coal-gasification gas streams, in chemically uncombined form (e.g. atomic form) and in chemically combined form (e.g. alkali metal salts such as, for example, the carbonates, chlorides, and sulfates) in amounts corresponding to from about 1 to about 5000 parts per billion by weight of alkali metal per se in the flowing gas mixture. For such applications, the filament may have a diameter from, e.g. about 0.001 to about 0.010 inch, preferably about 0.005 inch. The screen holes are preferably distributed substantially uniformly throughout the surface of the screens with the total open surface of the holes constituting about 10% to about 99%, preferably about 95%, of the overall area of the screen, i.e. the total area of the solid surface plus the surface area of the holes. The screen may be, for example, of about 15 to 30-guage wire with generally parallel strands thereof spaced apart a distance of about 1/16 to about ¼ inch.

The preferred HVDC source is a regulated power supply. The HVDC source preferably is provided with a voltage regulator (not shown) to maintain a substantially constant output voltage.

The total resistance of the biasing circuit leg connecting the positive terminal of the HVDC source to an end of the filament may be from about 0.01 to about 2 ohms, preferably about one ohm. The total resistance of the circuit connecting the screen to the positive terminal of the ammeter may be from about 0.01 to about 2 ohms, preferably about one ohm. The ammeter will supply a resistance of from about 1,000 to about 1,000,000 ohms, preferably about 300,000 ohms, whereby the ammeter detecting range will be from about $10^{-12}$ to about $10^{-6}$ amp, preferably about $10^{-9}$ amp. The LVHC source will preferably be a battery connected with its positive end to the same end of the filament which is connected to the positive end of the HVDC source. The LVHC source will have a voltage output of from about 2 to about 15 volts, preferably about 8 volts. The resistance of the circuit connecting the positive end of the LVHC source to the filament may have a resistance of from about 0.01 to about 2 ohms, preferably about one ohm. The portion of the LVHC circuit connecting the negative end thereof to an opposite end of the filament may have similar resistance characteristics, whereby the current flowing through the LVHC source circuit will be from about 1 to about 5 amps, preferably about 3 amps.

The resistance of the metallic sleeve is low, e.g. from about 0.01 to about 0.1 ohm, preferably about 0.05 ohm. The resistance of the ceramic sleeve 52 is high, e.g. from about $1 \times 10^6$ ohms to about $10 \times 10^6$ ohms, preferably about $5 \times 10^6$ ohms. The resistance of the PTFE sleeve is high, e.g. from about 1,000 to about 10,000 ohms, preferably about 5,000 ohms.

The spacing of the screen from the filament may be from about ¼ to about ½ inch, preferably about ⅜ inch. The platinum filament will preferably be substantially free of alkali metal. Substantial freedom from alkali metal can be effected by baking the filament at a temperature of about 1100° C. for about 24 hours.

The filament may be extended across a diameter of the pipe or across any other segment thereof as desired. However, extension across a pipe diameter is preferred.

Figure 3:
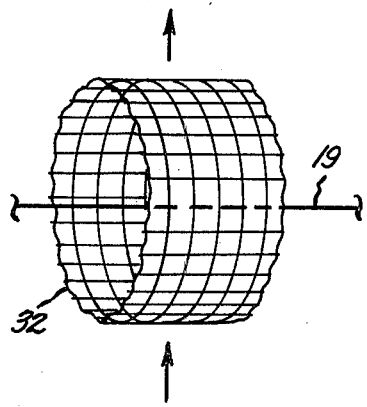
FIG. 3 is a fragmentary perspective view of a portion of the device.

In operation, as illustrated in FIG. 3, the gas flow is preferably conducted in generally perpendicular direction relative to the direction of the filament. With the LVHC and HVDC sources energized and connected as shown, a continuous signal is generated by the ammeter. Calibration of the device for a known concentration of alkali metals selected from the group consisting of sodium, potassium, and cesium, for the known flow rate of the gas being measured, permits generation of a plot of total alkali metal versus current signal. By reference to such plot, the total amount of alkali metal in the gas stream being measured can be determined from the current signal at any given instant during measurement.

The alkali metals which can be detected by this device include those alkali metals having an ionization potential of less than the work function of the filament. Compounds of the foregoing alkali metals having ionization potentials of less than this work function can also contribute to the detectable alkali metal content of the gas stream being measured.

In an experimental test of the instant device, the following dimensions and properties thereof and operating conditions were used: electrically grounded stainless steel pipe (4-inch inside diameter); stainless steel screen (15-mil diameter wire; ⅛ inch openings, 1-inch screen diameter); HVDC output (600 volts); LVDC filament-heater current (2 amps); platinum filament (0.005 inch in diameter and 2.75 inches in length); and gas stream velocity (one cm/sec). Potassium carbonate ($K_2CO_3$) aerosol was injected into the following nitrogen gas stream, resulting in an ammeter output signal of about $5.39 \times 10^{-9}$ amp per one part by weight potassium per million parts by weight gas over a range of $K_2CO_3$ concentration.

BEST MODE CONTEMPLATED

The best mode contemplated for carrying out this invention has been set forth in the description above, for example, by way of setting forth preferred structural arrangements, electrical characteristics, materials of construction, compositions and operating conditions, including but not limited to preferred ranges and values of amounts and other unobvious variables material to successfully practicing (including making and using the invention in the best way contemplated at the time of executing this patent application.

It is understood that the foregoing detailed description is given merely by way of illustration and that many modifications may be made therein without departing from the spirit or scope of the present invention.

What is claimed is:

1. A device for detecting the presence of one or more alkali metals present in trace amounts in a flowing gas, comprising:
    (a) a conduit defining a cavity adapted to conduct a flow of said gas along a flow path extending through said cavity,
    (b) a generally straight metalliferous filament having a work function of at least 5.3 ev disposed within said cavity and extending transversely through said flow path,
    (c) means for heating said filament to a temperature sufficient to ionize a substantial portion of the alkali metals,
    (d) an electrically conductive ion-collection member including a portion surrounding said filament in closely spaced coaxial relationship therewith to define an ionization-collection region of said cavity, said surrounding portion having a plurality of through-holes adapted to pass at least a portion of said flow therethrough,
    (e) means electrically connected at one end thereof through a first lead to said filament and connected at the other end thereof through a second lead to said ion-collection member for developing a high-voltage electrical field within said region, said field having lines of force extending from said filament through said flow path to said surrounding portion of said member to effect contact of said ions with said collection member and neutralization of said ions thus contacted,
    (f) means operably associated with said second lead for generating a signal in response to said neutralization and proportional to the rate of neutralization, and
    (g) means for both (i) electrically insulating said ion-collection member from said first lead and (ii) reducing leakage current through said signal-generating means, said insulating-and-leakage reduction means including (A) a first electrically insulating high-resistance sleeve extending longitudinally of and peripherally about said first lead adjacent the end thereof adjoining said filament, (B) an electrically conductive low-resistance metallic sleeve extending longitudinally of and peripherally about said high-resistance sleeve, (C) a second electrically insulating high-resistance sleeve extending longitudinally of and peripherally about said metallic sleeve, and (D) means for electrically connecting said metallic sleeve to ground.

2. The device of claim 1, wherein said metallic sleeve extends beyond at least one of said first and second high-resistance sleeves toward said ionization-collection region.

* * * * *